United States Patent [19]

Ascher

[11] Patent Number: 5,017,140

[45] Date of Patent: May 21, 1991

[54] REMOVABLE AND DISPOSABLE EXTENSION FOR A LIGHT GUIDE OF A DENTAL CURING LIGHT AND ITS METHOD OF USE

[76] Inventor: Jay Ascher, 2871 Alfred Ct., Oceanside, N.Y. 11572

[21] Appl. No.: 352,115

[22] Filed: May 15, 1989

[51] Int. Cl.$^5$ .............................................. A61C 5/00
[52] U.S. Cl. .................................. 433/215; 433/229; 250/504 H
[58] Field of Search ............... 433/229, 215, 141, 29; 250/504 H

[56] References Cited

U.S. PATENT DOCUMENTS

| | | | |
|---|---|---|---|
| 4,204,328 | 5/1980 | Kutner | 433/29 |
| 4,445,858 | 5/1984 | Johnson | 433/229 |
| 4,666,405 | 5/1987 | Ericson | 433/229 |
| 4,666,406 | 5/1987 | Kanca | 433/215 |

FOREIGN PATENT DOCUMENTS 2300347 10/1976 France ............................... 433/141

Primary Examiner—John J. Wilson
Assistant Examiner—Michael Lynch
Attorney, Agent, or Firm—Ladas & Parry

[57] ABSTRACT

A removable and disposable extension for a light guide of a dental curing light in which a hollow empty body having a calibrated aperture therein is detachably fitted on the rigid light guide so that the aperture faces the optical glass in the light guide. The hollow body is opaque to light and provides a pathway for light from the optical glass to and through the aperture. The aperture is calibrated so as to be of relatively small size compared to the optical glass to permit a relatively narrow beam of light to exit from the aperture. The extension permits substantially instantaneous spot curing of a composite between a laminate and a tooth to preserve their relative position when other operations are carried out.

14 Claims, 2 Drawing Sheets

REMOVABLE AND DISPOSABLE EXTENSION FOR A LIGHT GUIDE OF A DENTAL CURING LIGHT AND ITS METHOD OF USE

FIELD OF THE INVENTION

The invention relates to removable and disposable extensions for a light guide of a dental curing light and to its method of use.

BACKGROUND

In the current practice of dentistry, it is common to bond porcelain or acrylic laminates (also known as veneers) to the teeth for cosmetic and other purposes. The popularity of this procedure is due to its relative simplicity, its excellent results and the minimization of trauma to the existing teeth.

In effecting a bonding procedure, the laminate, which is relatively delicate as it is only about ½ mm thick, is seated on an etched tooth to which a so called composite resin and bonding agent has been applied. The bonding materials are light sensitive and are cured by light from a visible curing light. The period of time for curing is about 30 seconds. During this time, it is essential that the laminate remain in place and not be shifted as otherwise it may become necessary to remove and destroy the now bonded laminate and reprepare the tooth for the fabrication of a new laminate and new bonding operation.

Curing lights are known for bonding composites which include a hand held light gun with a curing probe or light guide on the gun for producing a beam of light for curing the composite. The light guide comprises a rigid outer body in which an optical ground glass body is fitted and fixed. It is known to provide a releasable connection between the gun and the light guide so that the light guides are provided in a variety of different sizes and shapes including straight light guides of 13 mm diameter for bonding large facial surfaces, light guides with bent ends for posterior curing of 8-13 mm diameter, light guides with less bent ends of 8 mm diameter for general curing purposes, and light guides with sharply bent ends for posterior layer curing of between 2 and 5 mm. Light guides of different size and shape can be fitted to the same light gun.

It is also known to directly connect a wand type light guide to a light generator and eliminate the gun in order to reduce weight and simplify the operation.

For sanitary purposes, the light guides can be autoclaved.

SUMMARY OF THE INVENTION

An object of the invention is to provide means and a method which will permit spot curing of a composite in a very short time to provide a firm and rapid connection of a laminate to a tooth before complete bonding of the entire laminate is effected.

A further object of the invention is to provide means and a method to achieve the spot curing in a sanitary fashion.

Yet another aspect of the invention is to effect the spot curing utilizing existing curing lights.

Another object of the invention is to provide disposable sanitary accessories to achieve the spot curing.

The above and further objects are satisfied according to the invention by the provision of a removable and disposable extension for a light guide of a dental curing light, the light guide having a rigid body with an optical glass fixedly fitted in the body, said extension comprising a hollow empty body having an aperture therein and means by which said body can be detachably fitted on the rigid body of the light guide such that the aperture in the hollow body faces the optical glass in the light guide. The hollow body is opaque to light and provides a pathway for light from the optical glass to and through the aperture. The aperture is of relatively small size compared to the optical glass to permit a relatively narrow beam of light to exit from said aperture.

In order to achieve the spot curing of the composite in a relatively short time, the aperture is sized between 1½ and 2 mm.

The hollow body is disposable after a single use and is preferably made from a plastic material which can be elastic and of tapered form so that it can be elastically fitted on and removed from light guides of wide ranging diameters.

In one embodiment of the invention, the extension includes internal inwardly projecting means for releasably engaging the rigid body of the light guide. The internal inwardly projecting means provides flexible gripping of the light guide so that the extension can be adapted to light guides of different diameters.

The invention further contemplates a method for effecting sanitary spot curing of composites joining laminates and teeth which includes the following steps:

placing a removable sanitary extension on a rigid body of a light guide for curing an adhesive joining a laminate and a tooth, forming said extension as a hollow body with an aperture which is spaced from the light guide in the path of the output beam when the extension is placed on the rigid body, the hollow body being light opaque and the output beam of light from the light guide being reduced in size upon exiting from the hollow body via said aperture, the beam of light exiting from the hollow body being sized for effecting spot curing of the resin joining the laminate and tooth, and removing the extension from the rigid body of the light guide after the spot curing to enable the entire laminate to be bonded to the tooth by the output beam from the light guide.

DETAILED DESCRIPTION OF PREFERRED EMBODIMENTS

Figure 1:
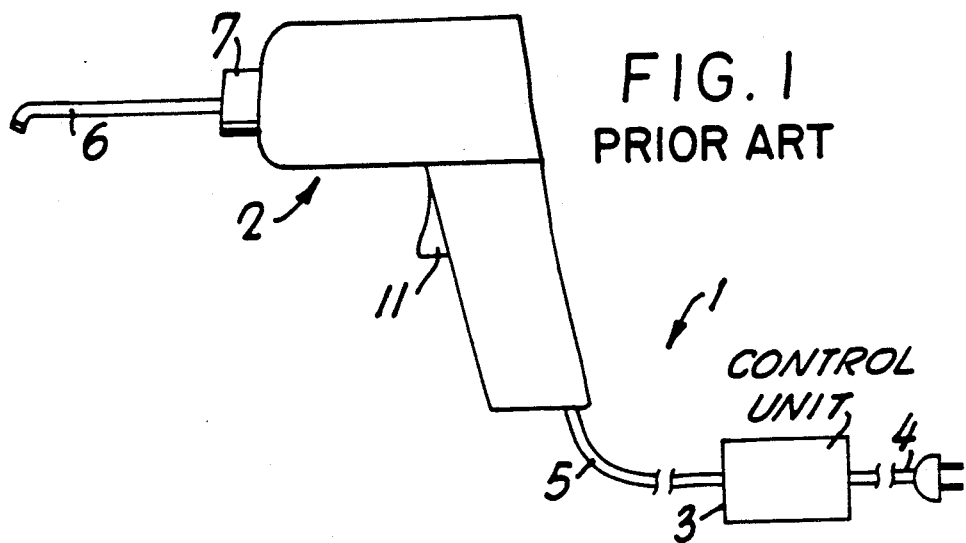
FIG. 1 is a diagrammatic illustration of a curing light of conventional design.
Figure 2:
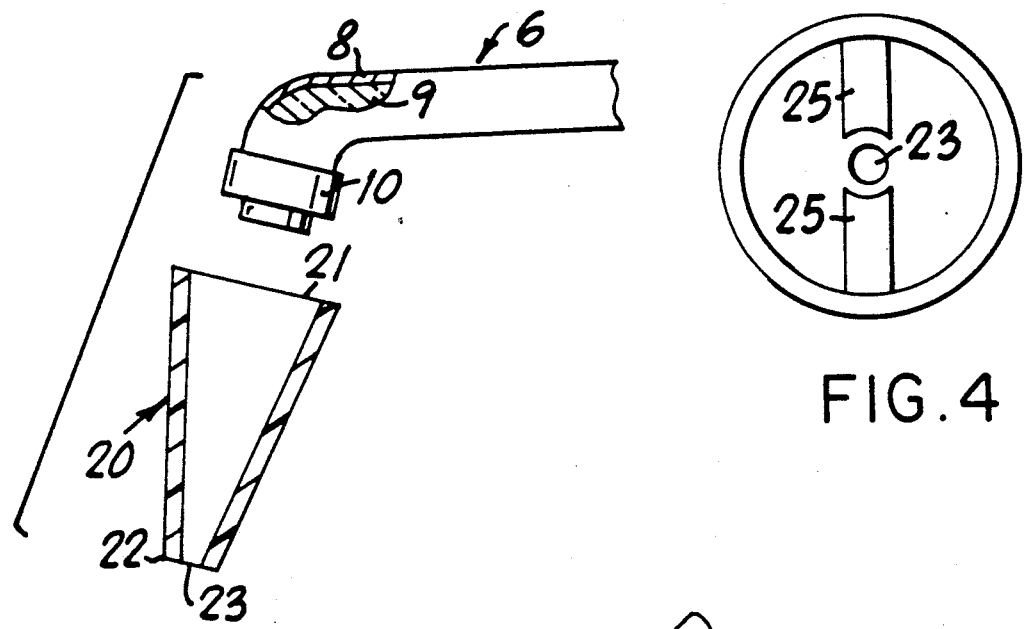
FIG. 2 shows a portion of the curing light of FIG. 1 with a sectional view of one embodiment of the invention on enlarged scale.

Referring to FIG. 1, therein is seen a visible curing light 1 for curing a composite for bonding laminates to teeth. The curing light 1 includes a gun 2 which is connected to a control unit 3 including a light generator which has a power cord 4 for connection to a power supply. The control unit 3 is connected to the gun 2 by a flexible power card 5. The light guide 6 is constructed as shown in FIG. 2 with a rigid outer body 8 in which an optical glass body 9 is fixedly fitted. A protective plastic tip 10 can be replaceably fitted on the end of the light guide 6.

In use, the control unit is activated by a switch (not shown) after the dentist brings the end of the light guide 6 on the tooth to be covered after a composite consisting of resin and bonding agent has been applied to the tooth. By activation of a trigger 11 on the gun 2, the light beam is passed to the light guide and therefrom onto the composite which becomes cured and hardened. Thereupon the laminate becomes bonded to the tooth. The laminate is sufficiently translucent or transparent to enable passage of the light beam therethrough to the composite. Normally, the time for curing is of the order of 30 seconds. The light guide 6 is replaceable with different size light guides to compensate for different size laminates. All light guides are composed of rigid outer body 8 with glass body 9 fixedly fitted therein.

In order to provide a measure of sanitary control, the tip 10 is replaceable on the end of body 8 of the light guide. Also, the light guide can be autoclaved and hence rendered sterile for the next use.

Since the curing light is fairly bulky and must be held for 30 seconds in place in proximity to the laminate, there is the danger that the laminate may be physically contacted and displaced from its seated position on the tooth. This is most undesirable as the entire restoration may then need to be completely redone.

The invention seeks a method and means by which substantially instantaneous spot curing of the composite can be effected so that the laminate will be reliably bonded to the tooth so that curIng of the remainder of the composite can be carried out wIthout danger of dislodging the laminate. Furthermore, by virtue of the spot bonding of the laminate to the tooth, the dentist is now permitted to carry out procedures on and in proximity to the tooth being restored, such as removal of any excess composite without danger of dislodging the laminate.

According to a first embodiment of the invention as shown in FIG. 2, there is provided a tapered sleeve 20 of conical shape whose larger end 21 can be fitted over the end of the light guide 6 until it is secured thereon in replaceable fashion. The opposite end 22 of the sleeve 20 has a calibrated aperture 23 thereat which is positioned in front of the end of the light guide 6 when the sleeve 20 is fitted on the light guide. More specifically, the aperture 23 faces the ground glass body 9. The sleeve 20 is made of a material which is opaque to light and provides a pathway for light from the optical glass 9 to and through the aperture 23.

The aperture 23 is calibrated to be of relatively small size compared to the diameter of the optical glass 9 to permit a relatively narrow beam of light to exit from the aperture 23. By virtue of the narrow beam of light which exits from aperture 23, substantially instantaneous curing of a tiny area of composite can be effected. This can be carried out at a number of strategic locations so that the laminate will become bonded to the tooth at a plurality of "spot-cures" to provide sufficient connection between the laminate and the tooth and enable the dentist to carry out operations on the laminate and tooth and regions in proximity thereto, such as clean any excess composite from the laminate and the tooth before the final curing of the remainder of the laminate is effected. Because of the spot cures, the laminate will be held in position to enable the dentist to carry out these tasks. After the spot curing has been effected and the procedure is to be continued, the sleeve 20 is removed from the light guide 6 and disposed of. The complete curing can then be effected in normal fashion with the normal light guide.

By virtue of the tapered configuration of sleeve 20, it is adaptable for application onto light guides of different diameters. The sleeve 20 can be individually packaged in sanitary condition to provide substantially safe conditions during the spot curing operation.

The tubular sleeve 120 is preferably made of a plastic material which has sufficient elasticity to allow it to be fitted onto the end of the light guide and to be frictionally engaged therewith. The plastic can be a heavy latex, polycarbonate, polyethylene, etc. The sleeve 20 has a thickness of about 2 mm, and this can be varied depending on the nature of the plastic as long as the body has sufficient rigidity to be self-supporting in shape when fitted on the light guide. The sleeve 20 has a length of about 20 mm and at its large end 21, it has a diameter of between 15 and 16 mm. The crucial dimensIon for the tubular sleeve is the diameter of the calibrated aperture 23 which, as previously indicated, is between 1½ and 2 mm.

Instead of gun 2, it is also known to employ the light guide as a wand unit with a modified control unit 3 to which it is directly connected. The tubular sleeve 20 of the invention is used in the same manner with this type of wand unit as well.

Figure 4:
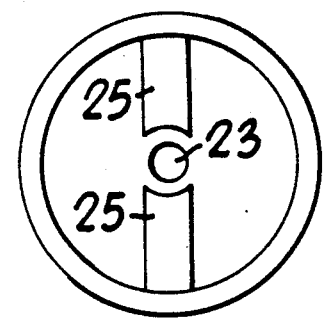
FIG. 4 is an end view of the embodiment in FIG. 3 taken on line 4—4 therein.
Figure 3:
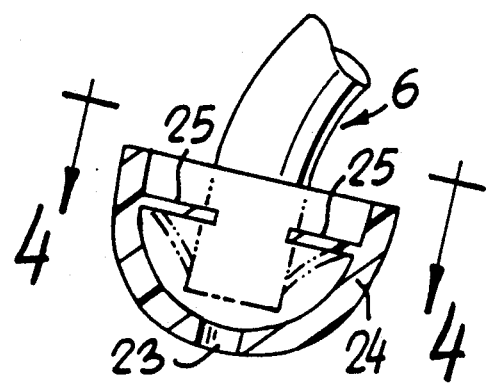
FIG. 3 shows another embodiment of the invention on enlarged scale.

Another embodiment of the invention is shown in FIGS. 3 and 4. In these figures, instead of tubular sleeve 20 of the removable and disposable extension, a body 24 is provided which has calibrated aperture 23 therein. Extending inwardly of the body 24 are internal projecting prongs 25 which are bendable and serve as means for releasably engaging the rigid body 8 of the light guide 6. This is clear from the dotted outline in FIG. 3 showing insertion of the light guIde 6 into the interior of the body 24 with frictional engagement of the prongs 25 which are bendable deformed and grip the outside surface of the guide 6. By virtue of the flexibility of the prongs 25, they serve as flexible gripping means capable of detachably engaging light guides of different diameters. The mode of use of the cup-like body 24 is the same as that of the tapered tubular body 20. The prongs 25 also serve to keep the body 24 centered on the guide 6 so that the aperture 23 will substantially coaxially face the ground glass body 9 in the light guide. In the embodiment of FIG. 2, the flexibility of the tubular sleeve 20 allows an axial positioning of the extension on the light guide so that the aperture 23 will be substantially coaxial with the ground glass body 9 of the light guide.

Figure 5:
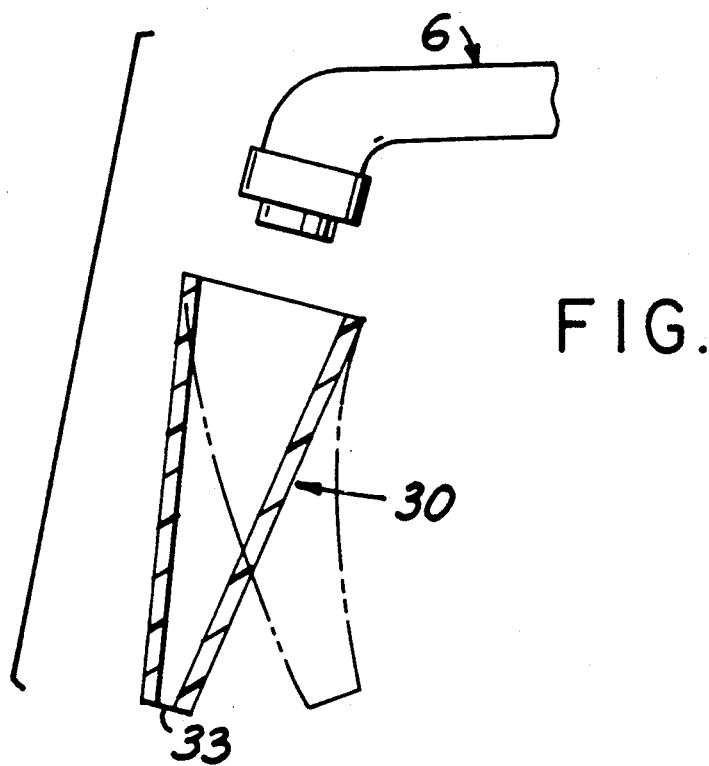
FIG. 5 is a view similar to FIG. 2 of a modified embodiment of the extension which can be bent as shown in dotted outline.

FIG. 5 shows a modified embodiment of the extension shown in FIG. 2 wherein tapered sleeve 30 is made of a flexible thermoplastic material of self sustaining shape. In this way the sleeve can be bent so that the calibrated aperture 33 can be aimed to a location to be spot cured. This gives the dentist increased capability in accessing regions heretofore not accessible. A bent configuration of the sleeve is shown in dotted outline in FIG. 5. Numerous thermoplastic materials are well known to those skilled in the art which can be bent and are self-sustaining in shape in the bent configuration. It is also well known to embed flexible wires of metal in the plastic to confer strength and shape retention for the material without substantially affecting its bendability.

Figure 6:
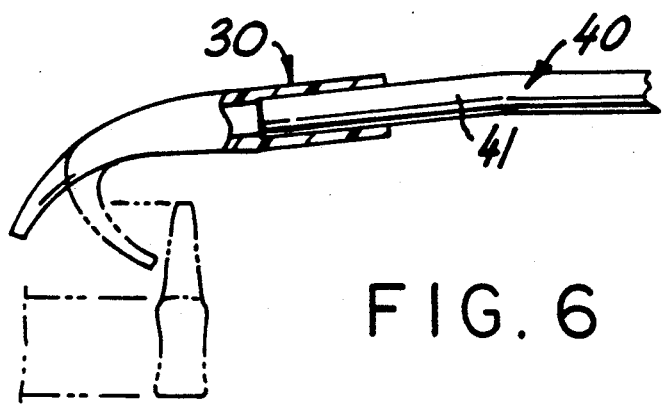
FIG. 6 is a view partly in section showing the extension applied to an air/syringe gun and in a bent configuration as shown in dotted outline to direct fluid to the lingual surface of a front tooth at the lingual gum line.

With this embodiment, the extension 30 has another utility as shown in FIG. 6 as an extension for an air/water syringe 40, especially for gaining access to lingual tooth surfaces particularly of the front teeth and distal tooth surfaces of molars. In this regard, conventional air/water syringes 40 have rigid tubular nozzles 41 which are relatively straight and do not enable the dentist to easily clean and dry these surfaces of the teeth, especially front teeth at the lingual gum line. With the shape-retaining flexible extension 30 of the invention, the dentist can bend the extension outside the mouth of the patient, and then insert the bent extension into the patient's mouth to direct a jet of air or water at the exact location desired. By way of example, in FIG. 6, the extension 30 is bent as shown in dotted outline and the outlet aperture of the extension faces the lingual gum line of a front tooth.

Although the invention has been described in relation to specific embodiments thereof, it will become apparent to those skilled in the art that numerous modifications and variations thereof can be made within the scope and spirit of the invention as defined in the attached claims.

What is claimed is:

1. A removable and disposable extension adapted for application to a light guide of a dental curing light and to a rigid air/water syringe, the light guide having a rigid body with an optical glass fitted in the body, the syringe having a rigid body for discharge of a fluid jet of air or water, said extension comprising a hollow empty body having an aperture therein, and means by which said body can be detachably fitted on the rigid body of the light guide or the rigid body of the syringe, said extension when fitted on said light guide having the aperture in the hollow body facing the optical glass in the light guide, said hollow body being opaque to light and providing a pathway for light from the optical glass to and through said aperture, said aperture being of relatively small size compared to the optical glass to permit a relatively narrow beam of light to exit from said aperture, said hollow body being tubular and made of bendable material which is self-sustaining in shape in a bent condition so that when the extension is fitted on the rigid body of the air/water syringe, the hollow body can be bent to direct a narrow jet of fluid to lingual surfaces of the front teeth and distal tooth surfaces of molars.

2. An extension as claimed in claim 1 wherein said aperture is between 1½ and 2 mm.

3. An extension as claimed in claim 2 wherein said hollow body is made of plastic material.

4. An extension as claimed in claim 3 wherein said hollow body is elastic.

5. An extension as claimed in claim 4 wherein said hollow body is in the form of a tubular sleeve.

6. An extension as claimed in claim 5 wherein said means which enables said body to be detachably fitted on the light guide comprises a tapered wall for the tubular sleeve which can be elastically fitted on and removed from the light guide and air/water syringe.

7. An extension as claimed in claim 2 wherein said means which enables said body to be detachably fitted on the light guide comprises internal inwardly projecting means in said body for releasably engaging the rigid body of the light guide.

8. A method of bonding a laminate to a tooth comprising applying a laminate to a tooth with a bondable resin between the laminate and the tooth, placing a removable sanitary extension on a rigid body of a light guide which produces an output beam of light for curing the resin joining the laminate and the tooth, forming said extension as a hollow body with an aperture which is spaced from the light guide in the path of the output beams when the extension is placed on the rigid body, the hollow body being light opaque and the output beam of light from the light guide being reduced in size upon exiting from the hollow body via said aperture, the size of the output beam exiting from the aperture in the hollow body being much smaller than the size of the laminate so that the beam of light exiting from the hollow body is sized for effecting rapid spot curing of the resin joining the laminate and tooth, removing the extension from the rigid body of the light guide after the spot curing, and irradiating the laminate and resin with the light exiting from the light guide, without the extension, to bond the entire laminate to the tooth by the output beam from the light guide.

9. A method as claimed in claim 8, said aperture passing an output light beam of 1½ to 2 mm in diameter.

10. A method as claimed in claim 8, said removable extension being placed on the rigid body of the light guide by frictionally engaging said extension with said light guide.

11. A removable and disposable extension for a light guide of a dental curing light, the light guide having a rigid body with an optical glass fitted in the body, said extension comprising a hollow empty body having an aperture therein, and means by which said body can be detachably fitted on the rigid body of the light guide such that the aperture in the hollow body faces the optical glass in the light guide, said hollow body being opaque to light and providing a pathway for light from the optical glass to and through said aperture, said aperture being of relatively small size compared to the optical glass to permit a relatively narrow beam of light to exit from said aperture, said hollow body being in the shape of a rounded cup, said means for detachably fitting the hollow body on the rigid body of the light guide comprising internal, radially inwards projecting means on said hollow body for releasably engaging the rigid body of the light guide.

12. An extension as claimed in claim 11 wherein said internal, inwardly projecting means comprises bendable prongs projecting radially inwards into the hollow interior of said cup-shaped hollow body and being dimensioned to undergo flexible bending to securely engage the hollow body on the rigid body of the light guide.

13. An extension as claimed in claim 12 wherein said hollow body is made of plastic material.

14. An extension as claimed in claim 11 wherein said radially inwards projecting means which enables said body to be detachably fitted on the light guide includes bendable gripping means capable of detachably engaging light guides of different diameters in a bent state.

* * * * *